United States Patent [19]

Stack et al.

[11] Patent Number: 4,867,156
[45] Date of Patent: Sep. 19, 1989

[54] PERCUTANEOUS AXIAL ATHEROECTOMY CATHETER ASSEMBLY AND METHOD OF USING THE SAME

[76] Inventors: Richard S. Stack, 6913 Falcon Bridge Rd., Chapel Hill, N.C. 27514; James H. McElhaney, 3411 Cambridge Dr., Durham, N.C. 27705

[21] Appl. No.: 66,344

[22] Filed: Jun. 25, 1987

[51] Int. Cl.⁴ .............................................. A61B 17/32
[52] U.S. Cl. .................................... 128/305; 128/754
[58] Field of Search ........................ 128/305, 751–755, 128/305.1, 310; 604/22

[56] References Cited

U.S. PATENT DOCUMENTS 4,099,529  7/1978  Peyman .............................. 128/305
4,771,774  9/1988  Simpson et al. .................... 128/305

FOREIGN PATENT DOCUMENTS 2044103  10/1980  United Kingdom ............... 128/305

Primary Examiner—Michael H. Thaler
Attorney, Agent, or Firm—Cushman, Darby & Cushman

[57] ABSTRACT

A percutaneous axial atheroectomy catheter assembly for circumferentially removing plaque from coronary arteries including first and second circumferential cutters for cutting first and second radial portions of plaque from the walls of an obstructed vessel and for receiving the excised plaque for removal from the targeted coronary artery.

15 Claims, 4 Drawing Sheets

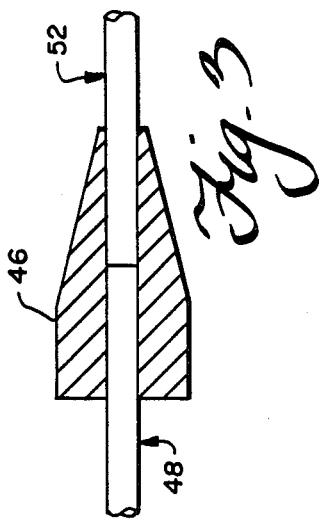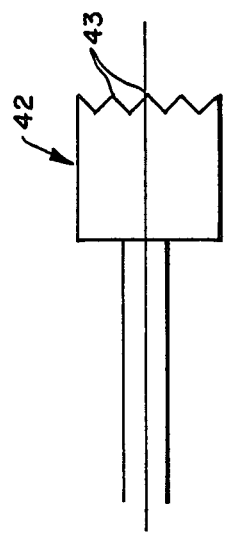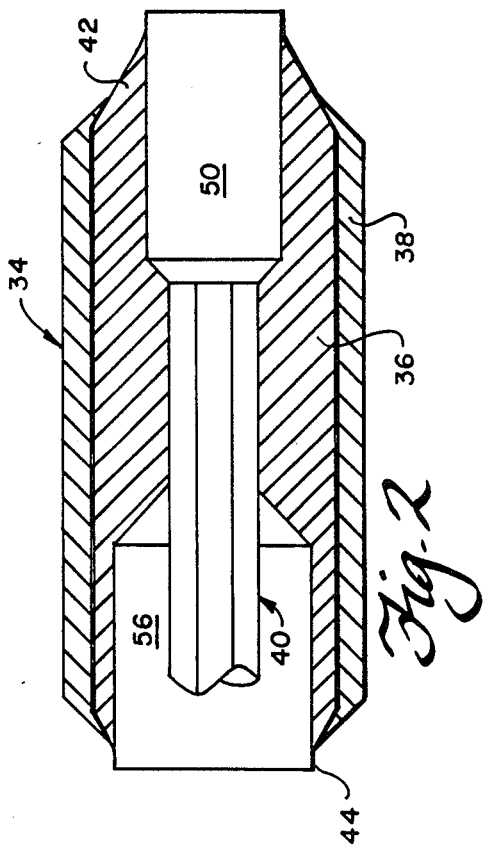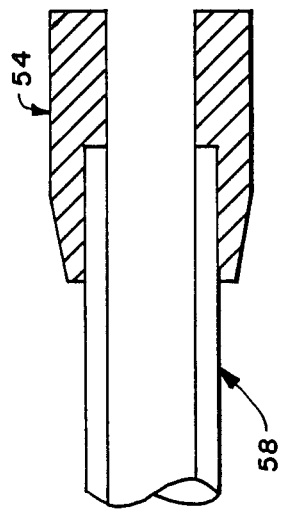

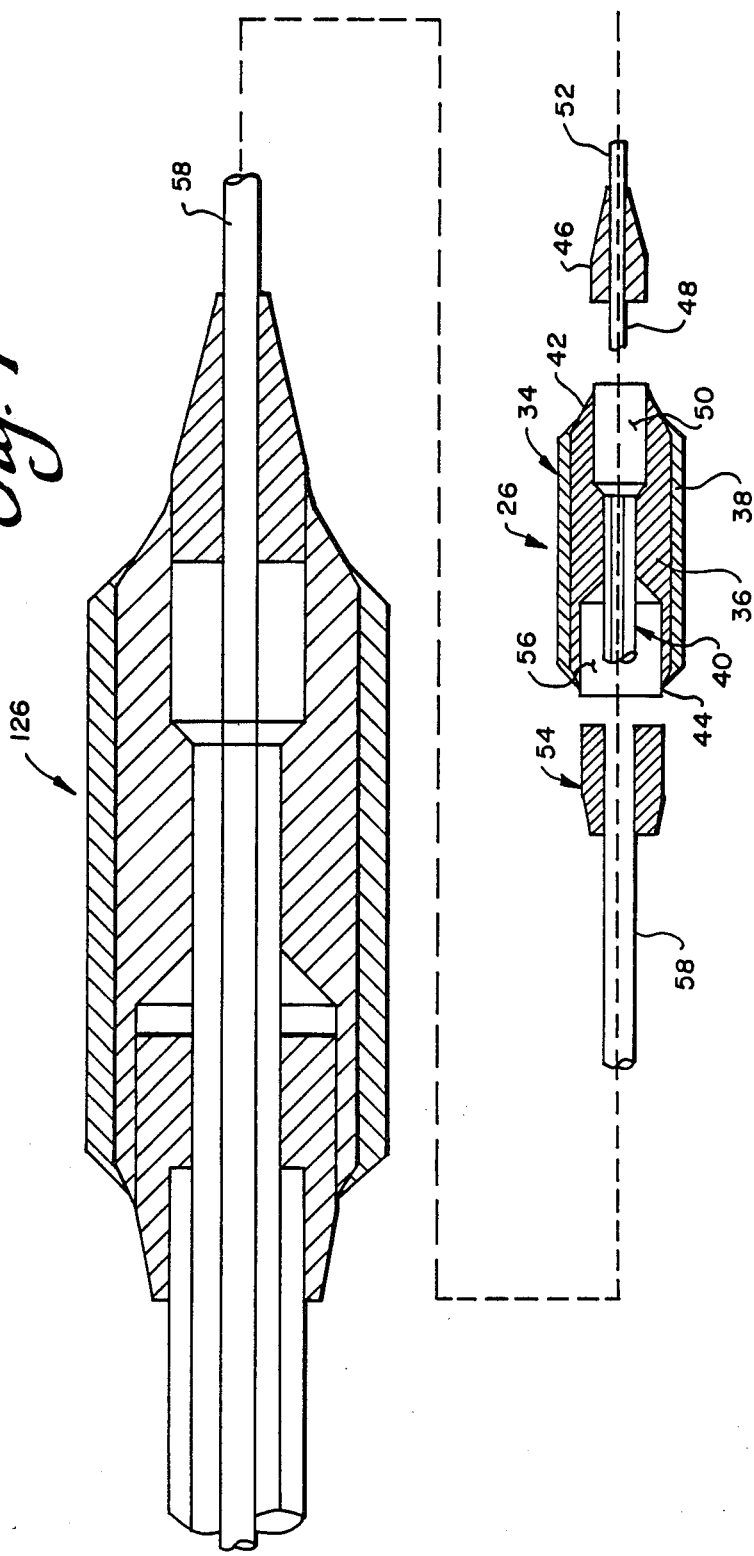

PERCUTANEOUS AXIAL ATHEROECTOMY CATHETER ASSEMBLY AND METHOD OF USING THE SAME

BACKGROUND OF THE INVENTION

This invention relates to coronary angioplasty and, more particularly, to a plaque-coring catheter assembly for removing plaque from coronary arteries.

A technique for coronary angioplasty has been developed which generally involves the use of a catheter system including a dilation catheter which is introduced, for example, via the femoral artery and advanced to the site of a stenotic lesion in a coronary artery. An extensible balloon mounted on the distal end of the dilation catheter is then inflated with a fluid. As the balloon is inflated, atherosclerotic material disposed on the vessel wall is compressed in a direction generally perpendicular to the wall of the vessel. This dilates the vessel to facilitate blood flow therethrough. While this technique has been rather successful in a number of instances, restenosis is common and, in the event the plaque cracks during expansion, subsequent collapse of the coronary artery is likely.

It would therefore be desirable to minimize the likelihood of restenosis of the vessel by removing at least a portion of the atherosclerotic plaque from the vessel rather than merely compressing the plaque. One manner in which the foregoing can be achieved is by guiding an catheter through the vascular system to the locus of a stenotic lesion and mechanically cutting the plaque from the vessel wall. Of course, once the plaque has been severed from the vessel wall, a means must be provided for removing the plaque from the vessel. This can be achieved, for example, by the provision of suction and lavage lumens in the catheter or by providing some structure to receive the severed plaque and carry same during removal of the catheter from the patient.

One such "atherectomy" catheter has been proposed and is currently under investigational use. This catheter is known as the Peripheral Simpson Atherectomy Catheter (P-SAC) manufactured by Devices for Vascular Intervention, Inc. (DVI). The P-SAC is designed to excise atheromatous material from diseased peripheral vessels after it has been percutaneously or intraoperatively introduced and directed to a target stenotic lesion by means of guide wire assisted navigation techniques. This catheter has several lumens and is equipped distally with a cylindrical cutter enclosed within a housing assembly. A balloon is positioned opposite an opening defined in the housing and is adapted upon inflation to urge the opening of the housing/cutter assembly against a target portion of atherosclerotic plaque. The cutter is then activated and is slowly advanced to excise the portion of the plaque extending through the opening into the housing interior. The cutter is designed to travel along the entire length of the housing and trap the excised material within the distal end of the housing. Upon completion of the cut, the balloon is deflated and the device is completely removed from the vessel.

While the above-mentioned catheter can effectively cut and remove given portions of plaque from the interior of a vessel wall, the device has a number of limitations. More particularly, the P-SAC device involves forcing a full diameter housing through the plaque at a stenotic portion of a vessel. Further, the longitudinally disposed balloon must be relied upon to force the plaque into the aperture on the side of the housing so that a limited amount of material from one side of the plaque can be removed. Thus, this process is likely to result in significant tearing of the plaque and vessel wall (dissection) as is the case with some of the standard angioplasty techniques. Indeed, the resultant trauma to the vessel wall could result in a reactive cellular proliferative response commonly seen with standard balloon angioplasty which results in a high incidence of restenosis at the site of the original lesion.

It would be desirable to provide a cutter that can circumferentially cut or excise plaque material from the vessel walls so that repeated removal and reinsertion of the atherectomy catheter to cut the plaque from about the circumference of the vessel are not necessary. It would also be desirable to provide a device which can excise a maximum amount of plaque once it is adjacent a target stenotic lesion so that repeated insertion and guiding of the device into the coronary arteries is minimized.

Further, it would be desirable to provide a plaque-coring catheter which can excise a maximum amount of plaque while minimizing the likelihood of lacerating the vessel.

SUMMARY OF THE INVENTION

It is therefore an object of the present invention to provide an atheroectomy catheter assembly which can circumferentially excise plaque from the interior of, for example, a coronary artery so that there is a uniform removal of plaque to form a smooth vessel interior and to minimize the need for repeated insertion and removal of the catheter.

It is another object of the catheter formed in accordance with the present invention to enable a maximum amount of plaque to be quickly and easily removed from the interior of a coronary artery.

These and other objects of the present invention are realized by providing a coring or circumferentially cutting atheroectomy catheter which preferably utilizes two cutting blades, one blade coring atherosclerotic plaque at a first diameter as the device is pushed or advanced through a stenotic region of the coronary artery and another blade for cutting plaque at a second diameter, greater than the first diameter, as the instrument is pulled back through the stenotic area.

Other objects, features, and characteristics of the present invention, as well as the methods of operation and functions of the related elements of the structure, and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

FIG. 2 is a cross-sectional view illustrating a pod-like cutting assembly formed in accordance with the present invention;

FIG. 3 is a cross-sectional view, partly broken away for clarity, showing a distal end cap of the pod-like cutting assembly of FIG. 2;

FIG. 4 is a cross-sectional view, partly broken away for clarity, of a proximal end cap of the pod-like cutting assembly formed in accordance with the present invention;

FIG. 6 is a elevational view of an embodiment of a cutting instrument formed in accordance with the present invention; and FIG. 7 is an elevational view of an alternate embodiment of an atheroectomy catheter assembly formed in accordance with the present invention.

DETAILED DESCRIPTION OF THE PRESENTLY PREFERRED EXEMPLARY EMBODIMENTS

Figure 1:
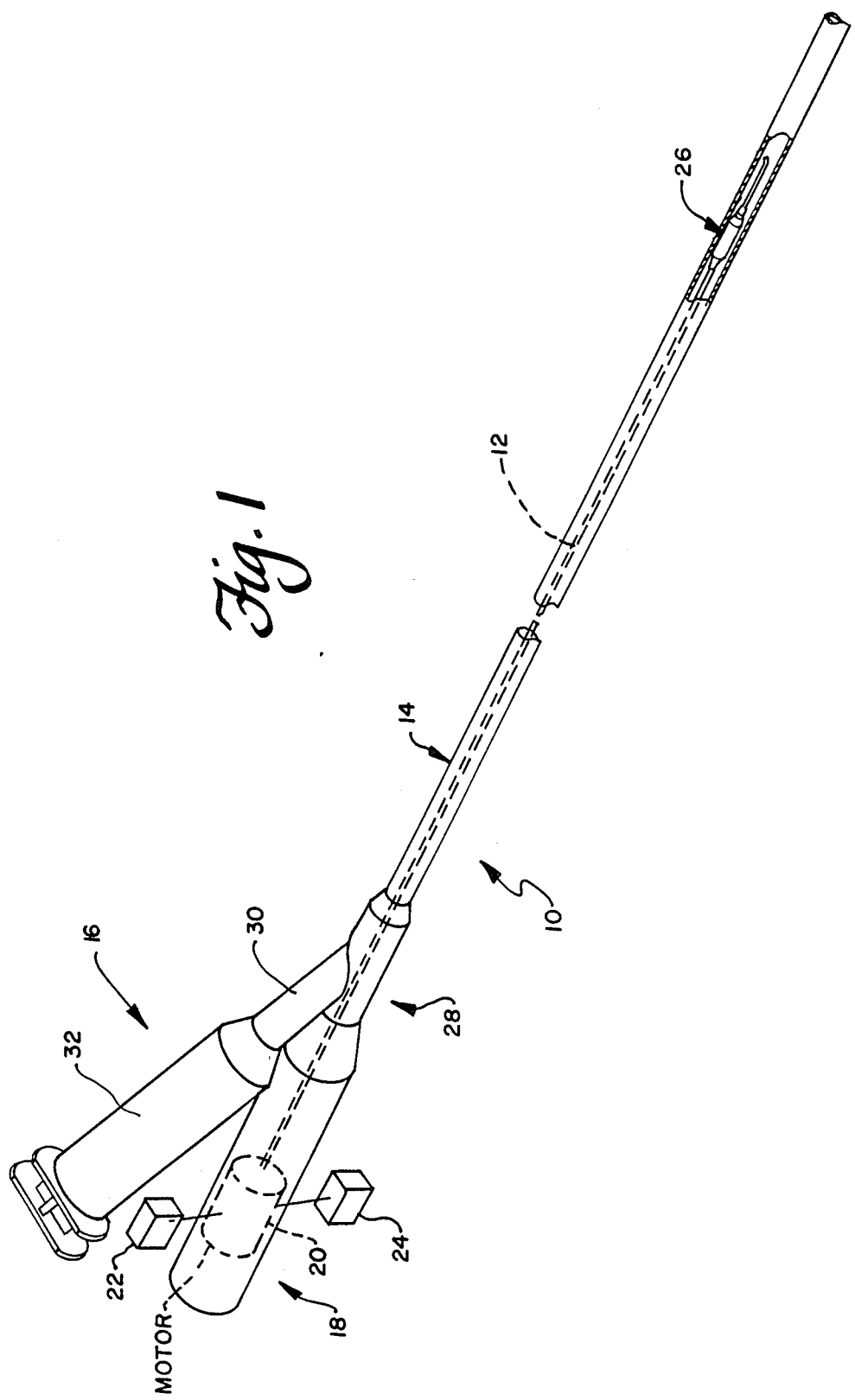
FIG. 1 illustrates an atheroectomy catheter assembly formed in accordance with the present invention.

Referring to FIG. 1, a percutaneous axial atheroectomy catheter assembly 10 formed in accordance with the present invention as shown. Catheter assembly 10 includes an atheroectomy catheter 12 slidably disposed within a guiding catheter 14. Guiding catheter 14 is provided to facilitate navigation of the major blood vessels leading to a target coronary artery. A hand operated control system 16 which includes a motor control section 18 having a drive motor 20 and switches 22 and 24 is operatively coupled to the pod-like cutting assembly 26 mounted on the distal end of atheroectomy catheter 12, as will be described more fully below. Further, suitable hand operated attachments (not shown) are mounted to each of the longitudinally extending elements of atheroectomy catheter 12 so that they can be separated from and coupled to the control section housing and independently advanced and retracted over one another for operation of the pod-like cutting assembly, which relative movement will be described more fully below.

A Y-connector 28 is preferably detachably mounted to the proximal end of catheter 14 to enable the injection of, for example, radiographic contrast liquids into guiding catheter 14 through side arm 30 with a syringe 32. Control section 18 is also detachably mounted to the proximal end of Y-connector 28 so that both control section 18 and atheroectomy catheter assembly 12 can be advanced and withdrawn through Y-connector 28 and guiding catheter 14.

Turning now to FIGS. 2–4, a pod-like cutting assembly 26 formed in accordance with the present invention is shown in greater detail. As can be seen, the main body portion 34 of pod-like cutting assembly 26 includes a core portion 36 rotatably mounted within an outer sleeve 38. Core portion 36 is rigidly coupled to drive cable 40 which is in turn operatively coupled to motor 20. Thus, when motor 20 is activated, drive cable 40 rotates to thereby rotate core portion 36.

Core portion 36 includes first and second cutting blade elements 42 and 44 on its distal and proximal ends, respectively. Distal cutting blade element 42, as can be seen in FIG. 2, has a diameter which is less than a diameter of proximal cutting blade element 44 so that atherosclerotic plaque can be sequentially cored at two different radii from a targeted stenotic portion of a coronary artery by a push-pull operation, as will be discussed more fully below with reference to FIG. 5a–e.

As can be further seen in FIG. 2, each of cutting blade elements 42 and 44 has a smoothly tapered outer surface which gradually increases from a smallest diameter immediately adjacent the cutting surface to a greatest diameter adjacent stationary sleeve 38 of pod-like assembly 26. Providing such a smoothly contoured exterior surface minimizes trauma to the vessel and the likelihood of cracking the plaque by gradually dilating that portion of the plaque which is not engaged by a particular cutting blade 42, 44 during the cutting operation.

Referring now to FIG. 3, a distal end cap 46 for the pod-like cutting assembly 26 formed in accordance with the present invention is shown. Distal end cap 46 is mounted to the distalmost end of a wire or cable 48 which is slidably received within drive cable 40. The proximalmost end of end cap 46 has an outer diameter corresponding to the inner diameter of distal cutting blade 42 so as to define a closed cavity 50 within the distal end of main portion 34, as will be discussed more fully below with reference to FIGS. 5a–e. A flexible guide wire 52 (FIGS. 1 and 5a–5e) is coupled to the distal end of cap 46 to facilitate navigation of the coronary arteries to the locus of a stenotic lesion. Finally, distal end cap 46 includes a forwardly tapered distal portion which, together with guide wire 52, facilitates the passage of end cap 46 through a stenotic region of a coronary artery, as will be discussed more fully below.

Turning now to FIG. 4, pod-like cutting assembly 26 also includes a proximal end cap 54. End cap 54 has a outer diameter corresponding to an inner diameter of proximal blade element 44. In this manner, proximal end cap 54 can engage rear blade element 44 to define a proximal chamber 56 within pod-like cutting assembly 26, as will be discussed more fully below with reference to FIGS. 5a–e. Finally, proxmial end cap 54 is coupled to a proximally extending tubular sheath 58 which is slidably received over drive cable 40 so that relative movement of proximal end cap 54, main body portion 34, and distal end cap 46 is possible. As will become more apparent below, relative movement of these components enables the realization of the advantageous cutting operation of the present invention. In addition, separation of these components as the atheroectomy catheter 12 is advanced to a target stenotic lesion facilitates navigation of sharply angulated portions of guiding catheter 14.

Figure 5A:
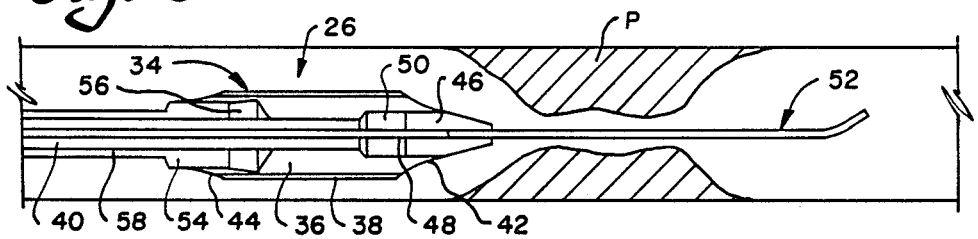
FIGS. 5a–5e illustrate the manner in which the catheter of FIG. 1 removes plaque from a coronary artery.

Turning to FIGS. 5a–e, the operation of the atheroectomy catheter formed in accordance with the present invention will be described in greater detail:

Pod-like cutting assembly 26, preferably with end caps 46 and 54 sealingly engaging cutting blade elements 42 and 44, respectively, is fed through guide catheter 14 (FIG. 1) to the target stenotic portion of the coronary artery. Once adjacent a proximal end of the stenotic region, catheter 12 is manipulated so that flexible guide wire 52 extends through the most restricted portion of the plaque P (FIG. 5a). Distal end cap 46 is then advanced through the restricted portion of the vessel by moving solid wire 48 distally to disengage end cap 46 from distal blade element 42. The smooth taper of end cap 46 gently deflects the plaque P as cap 46 passes through the stenotic portion. In this manner, the likelihood of "cracking" the plaque as the various portions of the pod-like assembly 26 pass through the stenotic portion is minimized.

Figure 5B:
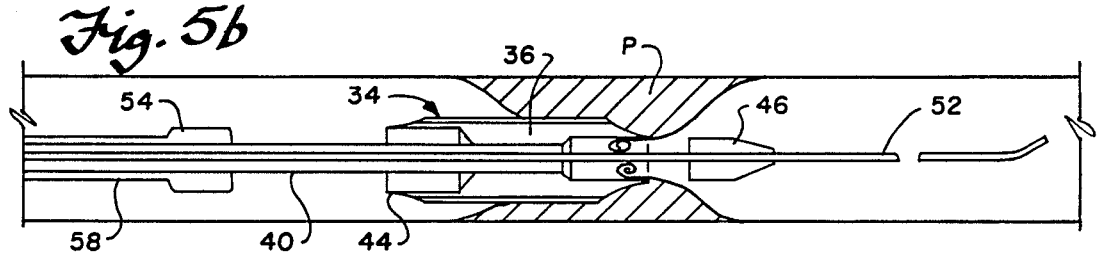
Figure 5C:
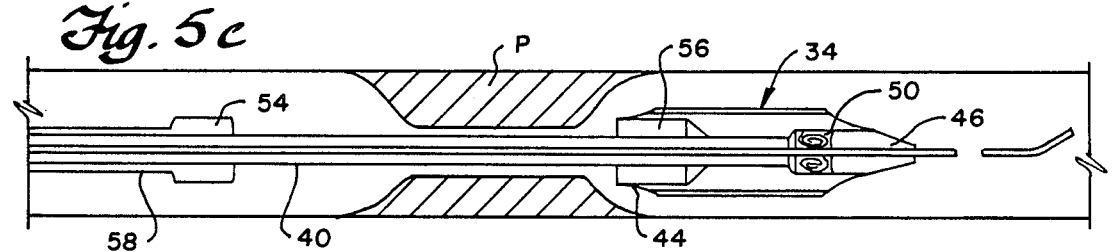
Figure 5D:
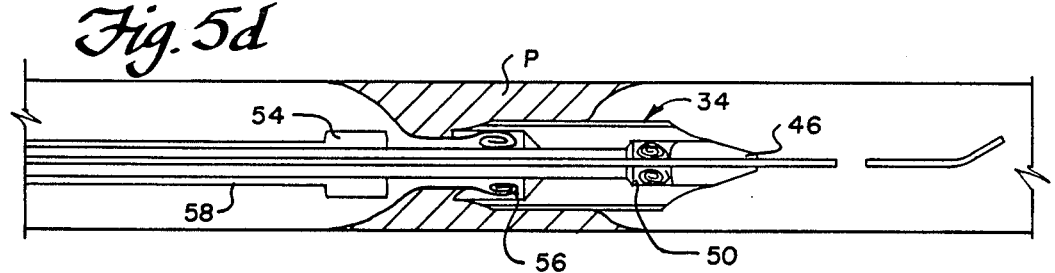
Figure 5E:
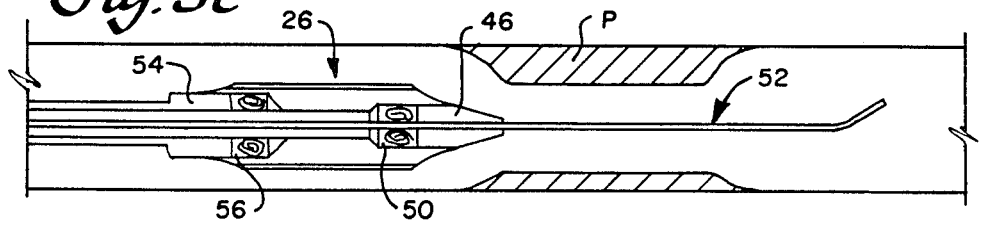

Once end cap 46 has been advanced beyond the targeted portion of the plaque P, core portion 36 is activated so that a circumferential portion of the plaque can be severed. More particularly, as can be seen in FIG. 5b, as cable 40 and core portion 46 rotate and pod-like assembly 26 is advanced, blade element 42 engages and circumferentially excises the plaque P from the vessel walls which is in turn captured in cavity 50. As can be further seen in FIG. 5b, when main portion 34 is advanced through the plaque it is disengaged from proximal end cap 54, as will be discussed more fully below. In addition, the tapered outer surface of blade element 42 deflects the plaque which is not engaged and cut by the cutting edge thereof to smoothly and evenly dilate the stenotic region and thus allow the remainder of pod-like assembly 26 to pass through the same with minimal resistance. Immediately after blade element 42 has cored the target stenotic region, the end thereof engages distal end cap 46 so that cavity 50 in the distal end of main portion 34 is closed and the plaque which has been excised by cutting blade 42 is sealed therein.

Once the pod-like assembly 26 has been pushed further so that it is disposed on the distal side of the stenotic region, the plaque which was displaced by the tapered surface of blade 42 tends to again extend inwardly and constrict the passage through the vessel. However, because end cap 54 was "left behind" on the proximal side of the plaque, proximal blade element 44 is exposed. Accordingly, by again activating core portion 36 so that it and proximal blade 44, coupled thereto, rotate and by pulling main portion 34 rearwardly through the stenotic region, the plaque can be further circumferentially cut. More particularly, because proximal blade element 44 has a greater diameter cutting edge than blade 42, another, larger, circumferential portion of the plaque can be excised from the vessel walls as main portion 34 is pulled rearwardly. As main portion 34 is pulled further rearwardly, blade 44 engages end cap 54 so that the excised plaque is captured and sealed within distal chamber 56. The entire pod-like assembly 26 can then be removed from the coronary artery and the procedure terminated or another atheroectomy catheter can be fed into the vascular system to remove plaque from another stenotic region.

While in the above-described embodiment the first and second cutting blade elements are substantially circular core-type cutters, it is to be understood that any suitable cutter that enables circumferential removal of plague from a vessel wall and capture of the excised plaque within the plaque receiving compartments of the pod-like main body portion 34 could be substituted for circular cutters 42 and 44. Furthermore, to maximize the cutting efficiency of the circular cutters, the cutting edges of the first and second blade may include cutting protrusions or teeth 43 as shown in the alternate embodiment of FIG. 6. Further, while in the illustrated embodiment the first and second cutting blades are mounted on the distal and proximal ends of the assembly 26 so as have their cutting edges extend distally and proximally, respectively, it is to be understood that these cutting blades may be mounted so that both are disposed so as to have their cutting edges facing distally.

In accordance with another embodiment of the present invention, a second pod-like cutting assembly 126 can be slidably disposed over sheath 58 to which end cap 54 is mounted so that an even greater diameter portion of the plaque can be removed from the vessel walls. More particularly, in this alternate embodiment, shown in FIG. 7, if larger diameter portions of the plaque are to be excised from the vessel walls, pod-like assembly 26 is advanced distally after the first push-pull excising procedure so that pod-like assembly 26 is disposed distally of the targeted stenotic region. Second pod-like assembly 126 is subsequently advanced over sheath 58 to the proximal side of the stenotic region. The second pod-like assembly can then be operated to excise third and fourth radial portions of the plaque from the vessel walls in a manner analogous to the operation of the first pod-like cutting assembly 26, described with reference to FIGS. 5a–5e.

As is apparent from the foregoing, then, the percutaneous axial atheroectomy catheter assembly formed in accordance with the present invention can excise first and second circumferential portions of the plaque so that a single complete cutting operation enables a maximum amount of plaque to be removed from the interior of a coronary artery, for example. Further, the plaque is permanently removed from the vessel interior so that rapid restenosis of the vessel wall is unlikely. In addition, the cutting operation performed in accordance with the present invention assures that the plaque severed from the vessel wall will be captured and contained so that the likelihood of embolus formation within the coronary vessel due to free floating severed plaque is minimized. Finally, following the cutting operation, the interior surface of the targeted region of the vessel is relatively smooth so that the unobstructed flow of blood therethrough is facilitated.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An apparatus for removing atherosclerotic plaque from the walls of a coronary artery comprising:

a housing member having a proximal end and a distal end;

first cutting means for circumferentially excising plaque from the wall of the artery at a first radius from a central axis of the artery, said first cutting means being mounted to one said ends of said housing member;

drive means operatively coupled to said first cutting means for driving said first cutting means;

first plaque receiving means defined within said housing member;

first seal means for sealing said first plaque receiving means slidably mounted to said housing member so as to be longitudinally displaceable relative to said housing member;

second cutting means for circumferentially excising plaque from the walls of the artery, said second cutting means excising plaque at a second radius from said central axis, greater than said first radius;

second plaque receiving mans defined within said housing member for receiving plaque excised by said second cutting means; and second seal means for sealing said second plaque receiving means slidably mounted to said housing member so as to be longitudinally displaceable relative to said housing member;

whereby, when said drives said first cutting means, plaque can be circumferentially excised from the walls of the artery and received in said first plaque receiving means, and, after a desired amount of plaque has been excised from the vessel wall, the first seal means can seal the first plaque receiving means and after said first cutting means has excised plaque from the walls of the artery at a first radius and said first seal means has sealed said first plaque receiving means, said second cutting means can circumferentially excise plaque from the walls of the artery at a second radius, the excised plaque being received in said second plaque receiving means, and, after a second desired amount of plaque has been excised from the vessel walls, the second seal means seals the second plaque receiving means.

2. An apparatus as in claim 1, wherein said first cutting means comprises a circular blade element mounted to said distal end of said housing member and said drive means is coupled to said housing member so as to rotate said first cutting means.

3. An apparatus as in claim 2, wherein said second cutting means comprises a circular blade element mounted to said proximal end of said housing member so as to be rotated by said drive means.

4. An apparatus as in claim 3, wherein said drive means comprises a tubular drive cable mounted to said housing member and said first seal means comprises a distal end cap which is slidably mounted to said housing member by means of a rigid wire element fixedly coupled to said distal end cap and slidably disposed within said tubular drive cable.

5. An apparatus as in claim 4, wherein said second seal means comprises a proximal end cap rigidly coupled to a sheath element slidably disposed over said tubular drive cable.

6. An apparatus as in claim 5, further comprising:
a second housing member having a proximal end and a distal end;
third cutting means for circumferentially excising plaque from the walls of the artery at a third radius from said central axis of the artery, said third cutting means being mounted to one of said ends of said second housing member;
drive means operatively coupled to said third cutting means for driving said third cutting means;
third plaque receiving means defined within said second housing member;
third seal means for sealing said third plaque receiving means slidably mounted to said second housing member so as to be longitudinally displaceable relative to said second housing member;
fourth cutting means for circumferentially excising plaque from the walls of the artery, said fourth cutting means excising plaque at a fourth radius from said central axis, greater than said third radius;
fourth plaque receiving means defined within said second housing member for receiving plaque excised by said fourth cutting means; and
fourth seal means for sealing said fourth plaque receiving means slidably mounted to said second housing member so as to be longitudinally displaceable relative to said second housing member;
said second housing member being slidably mounted to said sheath element so as to be slidable relative to the first housing member.

7. An apparatus as in claim 2, wherein said drive means comprises a tubular drive cable mounted to said housing member and said first seal means comprises a distal end cap which is slidably mounted to said housing member by means of a rigid wire element fixedly coupled to said distal end cap and slidably disposed within said tubular drive cable.

8. An apparatus as in claim 1, further comprising a sleeve element rotatably mounted to said housing member intermediate said proximal and distal ends.

9. An apparatus as in claim 1, wherein said second cutting means comprises a circular blade element mounted to said proximal end of said housing member and said drive means is coupled to said housing member so as to rotate said second circular blade element.

10. An apparatus as in claim 9, wherein said drive means comprises a tubular drive cable and said second seal means comprises a proximal end cap rigidly coupled to a sheath element slidably disposed over said tubular drive cable.

11. An apparatus as in claim 1, wherein said first seal means has a substantially planar proximal end.

12. An apparatus for removing material from the walls of a blood vessel comprising:
a housing member having a proximal end and a distal end;
first cutting means for circumferentially excising material from the walls of the blood vessel at a first radius from a central axis of the vessel, said first cutting means being mounted to one of said ends of said housing member;
second cutting means for circumferentially excising material from the walls of the blood vessel at a second radius from said central axis, said second radius being greater than said first radius;
drive means operatively coupled to said first and second cutting means for driving said first and second cutting means;
material receiving means defined within said housing member for receiving material excised by said first and second cutting means; and
seal means for sealing said material receiving means, said seal means being slidably mounted to said housing so as to be longitudinally displaceable relative to said housing member;
whereby, said first cutting means can excise material from the walls of the blood vessel at said first radius and then said second cutting means can excise plaque from the walls of the vessel at said second radius.

13. An apparatus as in claim 12, wherein said material receiving means include first and second material receiving means for receiving material excised by said first and second cutting means, respectively, and said seal means include said first and second seal means for sealing said first and second material receiving means, respectively.

14. An apparatus as in claim 12, wherein said first cutting means is mounted to said distal end of said housing member and said second cutting means is mounted to said proximal end of said housing member.

15. A method of removing plaque from the walls of a coronary artery comprising:
guiding an atheroectomy catheter to a stenotic portion of a coronary artery;
circumferentially excising plaque from the walls of the artery at a first radius from a central axis of the artery;
receiving the first radial portion of excised plaque in a first plaque receiving means defined within the housing member;
sealing the first plaque receiving mean so as to seal the excised plaque within the housing means;
circumferentially excising plaque from the walls of the artery at a second radius from said central axis;
receiving the second radial portion of excised plaque within a second plaque receiving means defined within the housing member;
sealing the second plaque receiving means so as to seal the excised plaque within the housing means; and
removing the atheroectomy catheter from the coronary artery.

* * * * *